United States Patent [19]

Schwarzmaier et al.

[11] Patent Number: 5,545,780
[45] Date of Patent: Aug. 13, 1996

[54] PROCESS FOR THE PREPARATION OF VINYL CHLORIDE

[75] Inventors: Peter Schwarzmaier; Peter Häckl, both of Kastl; Manfred Stöger; Ingolf Mielke, both of Burgkirchen, all of Germany

[73] Assignee: Hoechst Aktiengesellschaft, Germany

[21] Appl. No.: 385,280

[22] Filed: Feb. 8, 1995

[30] Foreign Application Priority Data

Feb. 12, 1994 [DE] Germany .................. 44 04 510.7

[51] Int. Cl.$^6$ .................................................. C07C 21/00
[52] U.S. Cl. ............................................................ 570/226
[58] Field of Search ............................................ 570/226

[56] References Cited

U.S. PATENT DOCUMENTS 3,860,595  1/1975  Kurtz et al. .................. 570/227
4,319,062  3/1982  Boozalis et al. .............. 570/220
4,417,964  11/1983 Rosdorf .
4,788,357  11/1988 Dummer et al. .............. 570/226

FOREIGN PATENT DOCUMENTS 0027554  4/1981  European Pat. Off. .
4142117  6/1993  Germany .

*Primary Examiner*—Alan Siegel
*Attorney, Agent, or Firm*—Connolly & Hutz

[57] ABSTRACT

The conversion rate in the preparation of vinyl chloride by thermal cracking of 1,2-dichloroethane is determined by measuring the absorption of high-energy radiation, the pressure and the temperature of the gases issuing from the cracking furnace.

7 Claims, No Drawings

PROCESS FOR THE PREPARATION OF VINYL CHLORIDE

Vinyl chloride (VC) is obtained by thermal elimination of hydrogen chloride from 1,2-dichloroethane (EDC), the conversion rate generally being kept at the order of magnitude of 60 % in order to keep the formation of by-products and, in particular, coke small. A conversion rate of about 60 % means that the gas mixture produced from the cracking—termed "cracking gas" below—is essentially a ternary mixture of VC, hydrogen chloride and EDC.

Determination of the cracking conversion rate by measuring the VC concentration in the cracking gas is associated with considerable difficulties, since connections for analytical determinations such as extractive measurements or, for example, for gas chromatographs rapidly become blocked by deposits. In practice therefore, measurement of the temperature at the outlet of the cracking furnace generally suffices, this measured value of temperature being used for control of the heating, for example the methane supply. In this manner, the starting temperature is kept as constant as possible.

It has been found that a certain scattering in the EDC conversion rate of about ±2% occurs owing to external influences even with constant starting temperature at the cracking furnace. This prevents maintenance of optimal reaction conditions and prevents the minimization of the by-product formation and of energy consumption.

The object underlying the invention is to keep the conversion rate in the EDC cracking furnace as constant as possible and as a result to suppress the formation of by-products and, in particular, coke formation. This object is achieved according to the invention by the control parameter determined being the absorption of high-energy, in particular radioactive, radiation, expediently at the outlet of the cracking furnace, for it has been found that the absorption measured is a measure of the density of the cracking gas and the VC concentration. If desired, the measured value, after appropriate calibration, can therefore also be expressed as density of the cracking gas or as VC concentration. This parameter can therefore be directly used for controlling the fuel supply for heating the cracking furnace.

The conversion rate determination according to the invention is advantageous especially when shared work-up takes place for a plurality of cracking furnaces operated in parallel. In this way, in the event of variation in conversion rate, it is possible to establish without problem in which of a plurality of furnaces the reaction is not proceeding as programmed.

The invention permits the exact measurement of the conversion rate and its maintenance or control. It thus effects a more reliable suppression of by-product formation, in particular coke formation, which in turn leads to considerably increased service lives of the entire plant.

The radiometric measurement of foam density has already been used to determine the degree of conversion of a polymerization (DE-A 41 42 117). For this purpose a latex sample from the polymerization vessel is depressurized in a measurement tube and the foam thus formed is radiometrically radiated. The attenuation of γ-rays occurring on transmission through the medium to be measured is, in accordance with the Lambert-Beer law, a measure of density. For a constant measurement path length, the residual radiation still arriving at the detector is thus a measure of the density of the product to be measured. However, this measurement method described does not permit continuous monitoring of the conversion rate.

The radiometric measurement according to the invention is performed on cracking gas as follows: a heat-insulated S-shaped tube of a length of approximately 3000 mm serves as density measurement section, since it has been found that in the tube bends, only slight deposits occur so that the measurement is not impaired. A radioactive emitter, in particular a γ-emitter, and a receiver are therefore installed—opposite to each other—in the region of the tube bends. At the same time, pressure and temperature are measured in this tube section. The measured values "operating density", pressure and temperature are continuously recorded in a computer and corrected via calculation algorithms to give the standard density of the cracking gas. The conversion rate can be determined in the computer from this standard density.

Determination according to the invention of the EDC conversion rate is independent of the EDC cracking procedure. This is expediently performed with recovery of the cracking gas heat, for example by the processes of EP-A 21 381, 264 065 or 276 775.

The invention is described in more detail in the example below.

EXAMPLE

The cracking gas (essentially comprising EDC, VC, HCl, but also traces of by-products) issuing from the EDC cracking furnace is passed into a heat-insulated, S-shaped bent tube piece approximately 3000 mm long. An emitter and receiver for γ-radiation are mounted at opposite tube bends.

The continuously measured γ-ray absorption, the pressure and the temperature are passed to a data processing unit where the operating density is determined from these measured values. In an analog-digital converter, the operating density is corrected to give the standard density. The conversion rate is determined therefrom via a further iterative computation method. This conversion rate serves as a controlled variable for the fuel supply.

We claim:

1. A process for the preparation of vinyl chloride by thermal cracking of 1,2-dichloroethane, which comprises passing the effluent from a 1,2-dichloroethane cracking furnace into a radiometric measurement zone and passing high-energy radiation through said effluent; measuring the adsorption of said radiation; determining the conversion to vinyl chloride in said cracking furnace by the degree of adsorption of said radiation; and maintaining a desired conversion to vinyl chloride in said cracking furnace based upon said adsorption.

2. The process as claimed in claim 1, wherein radioactive radiation serves as the high-energy radiation.

3. The process as claimed in claim 1, wherein the attenuation of γ-rays occurring on transmission through the cracking gas is measured.

4. The process as claimed in claim 1, wherein the reaction is controlled via the fuel supply to the cracking furnace.

5. The process as claimed in claim 2, wherein the reaction is controlled via the fuel supply to the cracking furnace.

6. The process as claimed in claim 3, wherein the reaction is controlled via the fuel supply to the cracking furnace.

7. The process as claimed in claim 4, wherein the reaction is controlled via the fuel supply to the cracking furnace.

\* \* \* \* \*